United States Patent [19]
McGregor et al.

[11] Patent Number: 5,478,327
[45] Date of Patent: Dec. 26, 1995

[54] SURGICAL NEEDLE WITH DECREASED PENETRATION

[75] Inventors: Walter McGregor, Flemington; William McJames, Belle Mead, both of N.J.; William Schaeffer, Yardley, Pa.; Semyon Shchervinsky, Whitehouse Station, N.J.

[73] Assignee: Ethicon, Inc., Somerville, N.J.

[21] Appl. No.: 138,947

[22] Filed: Oct. 18, 1993

[51] Int. Cl.$^6$ ........................................ A61M 5/32
[52] U.S. Cl. ........................... 604/272; 604/239; 606/222
[58] Field of Search ....................... 606/222–227; 604/239, 272, 274; 223/102

[56] References Cited

U.S. PATENT DOCUMENTS

| | | | |
|---|---|---|---|
| 2,954,768 | 10/1960 | Hamilton | 604/274 |
| 3,094,123 | 6/1963 | Kurtz | 606/223 |
| 4,133,339 | 1/1979 | Naslund | 606/222 |
| 4,197,643 | 4/1980 | Burstone et al. | |
| 4,513,747 | 4/1985 | Smith . | |
| 4,660,559 | 4/1987 | McGregor et al. | |
| 4,672,734 | 6/1987 | Kawada et al. | |
| 4,799,484 | 1/1989 | Smith et al. | |
| 4,828,547 | 5/1989 | Sahi et al. | |
| 4,883,469 | 11/1989 | Glazier . | |
| 4,883,471 | 11/1989 | Braginetz et al. | |
| 4,905,695 | 3/1990 | Bendel et al. | |
| 5,100,432 | 3/1992 | Matsutani . | |
| 5,123,910 | 6/1992 | McIntosh . | |
| 5,178,607 | 1/1993 | Lynn et al. | 604/86 |
| 5,207,658 | 5/1993 | Rosen et al. | 604/272 |
| 5,342,397 | 8/1994 | Guido | 606/222 |

OTHER PUBLICATIONS

Abidin et al., Biomechanics of Curved Surgical Needle Bending, Biomed. Mater. Res. Appl. Biomaterials, vol. 23, No. A1, 129–143, (1989).
Bendel et al., Ophthalmic Needles, *Ophthalmology*, vol. 93, No. 9, (Sep. 1986).
McClung et al., Biomechanical Performance of Ophthalmic Surgical Needles, *Ophthalmology*, vol. 99, No. 2 (Feb. 1992).
Pavlovich, Lucas J., et al., A Synthetic Membrane for Testing Needle Penetration, *Journal of Applied Biomaterials*, vol. 4, 157–160 (1993).
Bendel, Lee P., et al., Tensile & Bend Relationships of Several Surgical Needle Materials, *Journal of Appl. Biomaterials*, vol. 4, 161–167 (1993).

*Primary Examiner*—C. Fred Rosenbaum
*Assistant Examiner*—N. Kent Gring

[57] ABSTRACT

A blunt tip surgical needle which significantly reduces the probability of skin penetration of the gloved hand of an operator is disclosed. The blunt tip needle includes a tip portion having at least one flat surface. The flat surface(s) blends smoothly between each other and with the outer surface of the tip portion such that the entire tip portion has a continuously smooth outer surface lacking any discontinuities or sharp edges.

5 Claims, 2 Drawing Sheets

SURGICAL NEEDLE WITH DECREASED PENETRATION

BACKGROUND OF THE INVENTION

1. Field of the Invention

This invention relates generally to surgical needles and, more particularly, to a blunt surgical needle wherein the needle tip portion has one or more flat surfaces which blend smoothly into the needle and decrease potential skin penetration of the gloved hand of an operator.

2. Description of the Prior Art

Everyone today is well aware of the severity of contracting Human Immunodeficiency Virus (HIV) and Acquired Immune Deficiency Syndrome (AIDS). The members of professions that must deal on a daily basis with the risk of coming in contact with people that do or may have HIV or AIDS are acutely aware of the severity. Members of the medical profession, especially surgeons, are in an extremely high risk position when performing operations. The knowledge that infectious diseases such as the AIDS virus can spread by an accidentally inflicted needle stick from a contaminated needle administered to the person having AIDS is the cause for much concern for the profession. These professionals are therefore taking every precaution to reduce the risks. For example, the use of double gloving, blunt tipped needles and gloves thickened at the fingers are known to reduce the rate of glove puncture. In addition, the use of forceps designed to grip both the tissue and needle more effectively and the use of staples for skin closure are also known to reduce the incidence of glove puncture.

Accordingly, there has been an increasing amount of activity in the area of surgical needle tip design. For example, U.S. Pat. No. 4,828,547 to Sahi et al. discloses a needle having a blunting member which is moveable from a retracted position to an extended position. In the retracted position, the blunting member does not interfere with the puncture tip of the needle. In the extended position, the blunting member extends beyond the puncture tip and therefor acts as a guard against accidental needle sticks. Further examples of shield or guard type assemblies for syringe needles are disclosed in U.S. Pat. Nos. 4,883,469 to Glazier and 4,883,471 to Braginetz et al.

The devices disclosed above are useful for hypodermic syringe needles which are disposed of after a single stick. This design would not be practical for use with surgical needles since such needles must make repeated sticks into the body.

U.S. Pat. No. 5,123,910 to Mcintosh discloses a tapered needle tip having a circular cross-section and terminating in a blunt head. The blunt head has a part spherical or other curved shape with no sharp edge surfaces. The problem with the prior art blunt head needles is the force necessary to penetrate the tissue is too high so that the momentum of the needle after it passes through the tissue is also so high that the needle penetrates the gloved hand of the surgeon thereby negating the safety factor of the blunt head. As a consequence, this blunt tip needle does not significantly reduce the probability of skin penetration of a gloved hand. Thus, there is a need to develop an improved surgical needle for use in suturing non-cutaneous and friable soft tissues of the body while at the same time significantly reducing the probability of skin penetration of the gloved hand of an operator.

SUMMARY OF THE INVENTION

The present invention is directed to a blunt tip surgical needle which significantly reduces the probability of skin penetration of the gloved hand of an operator thereby decreasing potential transmission of all infectious agents. The blunt tip surgical needles of the present invention include a tip portion which terminates in a blunt tip. Moreover, the tip portion has one or more flat surfaces that blend smoothly between each other and with the needle surface without any sharp edges. The provision of the one or more flat surfaces improves upon the prior art blunt tip needle in that the needles of the present invention are less likely to penetrate the glove and skin of the user. The needles of the present invention have a blunt tip to provide protection against penetration of a surgical glove and in addition includes the one or more flat surfaces on the side of the tip that allows for less penetration force through tissue. The force necessary to penetrate the tissue is, therefore, not excessive and the momentum of the needle after the penetration will not as in with prior art blunt tip needles overcome the bluntness of the tip and not penetrate the glove of the operator.

In one embodiment of the present invention, the tip portion of the needle has a flat pressed circular cross-section having two flat surfaces substantially throughout its entire length. The flat pressed circular tip portion terminates in a blunt head having a flat pressed circular dome shape. The curved blunt head and the two flat surfaces blend smoothly with the outer surface of the tapered portion such that the entire tip portion has a continuously smooth outer surface lacking any discontinuities or sharp edges. The blunt tip needle with flat side surfaces of the present invention has an increased resistance to penetration of a latex glove over a sharp point needle while at the same time decreasing the penetration force for non-cutaneous or friable tissue.

In another embodiment of the present invention, the tip portion of the needle has a triangular cross-sectional shape having three flat surfaces and rounded corners. The triangular cross-sectional shape of the tip portion progressively decreases toward its distal end and terminates in a blunt tip having a triangular dome shape. The blunt tip and the three flat surfaces blend smoothly with the outer surface of the tapered portion such that there are not sharp edge surfaces or discontinuities. As with the flat pressed circular embodiment above, the glove penetration resistance is increased while the friable tissue penetration force is decreased.

In another embodiment of the needle of the present invention, the tip portion has a circular cross-section which decreases progressively towards the distal end which terminates in a flat blunt tip. The flat blunt tip blends smoothly with the outer surface of the tapered portion such that there are no discontinuities or sharp edges. By having a flat surface on the needle tip, the resistance to penetration is increased over prior art rounded blunt tip needles.

As a result of having at least one flat surface, the needles of the present invention are a significant improvement in bluntness over conventional sharp point needles and blunt tip needles having no flat surfaces. The improved blunt tip surgical needle configurations of the present invention permit relatively easy penetration of soft non-cutaneous or friable body tissues while providing increased protection against a unintended stick of the gloved hand of an operator.

The needle of the present invention is suitable for use in suturing the liver, kidney, heart, muscle and fascia, adipose pericostal tissue and other non-cutaneous or friable soft tissues, as well as other types of tissue of the body, while simultaneously decreasing the probability of skin penetration of the gloved hand of an operator and operating personnel such as surgeons, surgeons' assistants, scrub and circulating nurses.

DETAILED DESCRIPTION OF THE INVENTION

Figure 1:
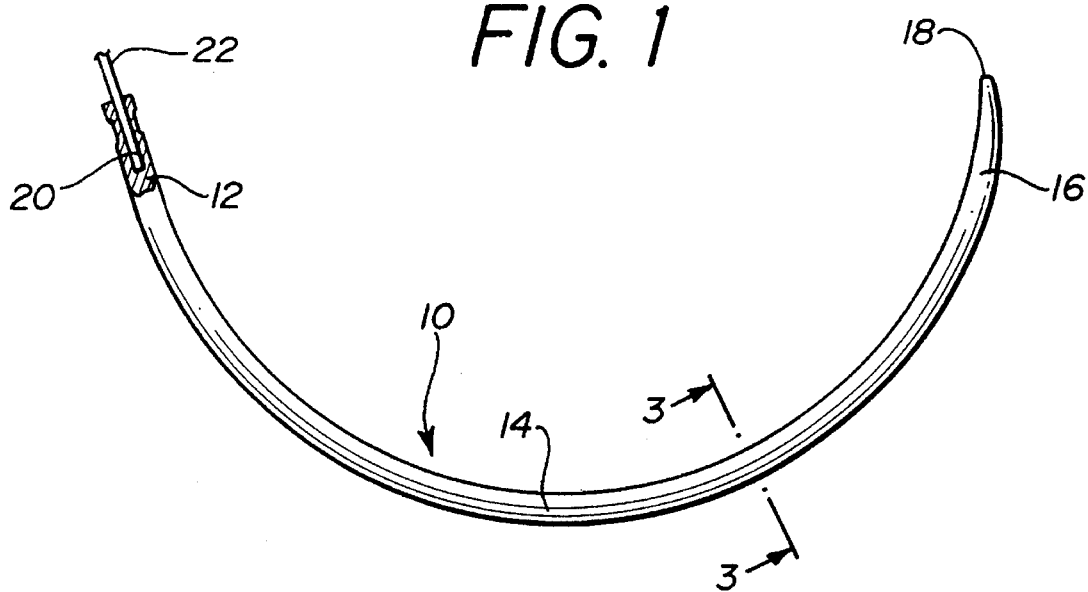
FIG. 1 is a perspective view of the blunt tip surgical needle of the present invention.

Referring to the drawings in FIGS. 1–5, there is shown one embodiment of the blunt tip surgical needle 10 of the present invention. The needle 10 includes a suture mounting portion 12, a contiguous main body portion 14 having a generally uniform cross-sectional area throughout an entire length thereof and a contiguous tip portion 16.

The suture mounting portion 12 is straight and has a hole 20 extending from a proximal end face of the suture needle along an axis thereof. The length of the suture mounting portion 12 is generally equal to or slightly greater than the length of the hole 20. A suture 22 is inserted at one end portion into hole 20 and then the suture mounting portion 12 is deformed or compressed to hold the suture 22.

Figure 3:
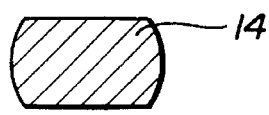
FIG. 3 is a cross-sectional view taken along lines 3—3 in FIG. 1.
Figure 4:
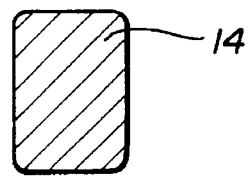
FIG. 4 is an alternative embodiment of the cross-sectional view taken along lines 3—3 in FIG. 1.

The cross-sectional shape of the main body portion 14 can have a wide variety of conventional shapes including circular, square and rectangular. However, in order to provide stability and control of needle 10 during use, the main body portion 14 can have a flat pressed circular cross section such as shown in FIG. 3 or, alternatively, a modified square cross-sectional shape as shown in FIG. 4. In the needle 10, the main body portion 14 and the tip portion 16 are curved and can possess a constant radius of curvature. This configuration is, however, not critical to the present invention and body portion 14 and tip portion 16 can therefore assume any straight and/or curved configuration which is considered suitable for the particular purpose that is intended.

The needle 10 is rigidly formed of a suitable material for suture needle use inside the body such as surgical grade steel, martersite-type stainless steel and precipitation hardened stainless steel.

Figure 2:
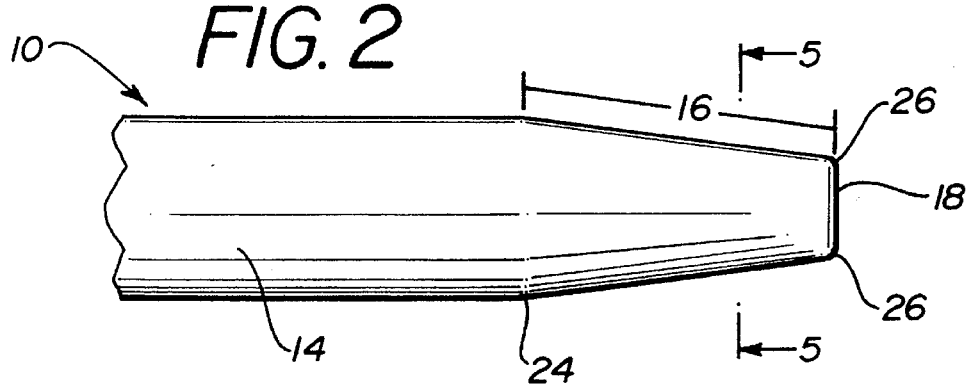
FIG. 2 is an enlarged fragmentary view of the tip portion of the surgical needle of FIG. 1.
Figure 5:
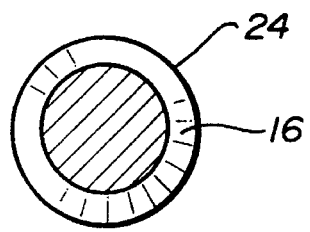
FIG. 5 is a cross-sectional view taken along lines 5—5 in FIG. 2.

Referring to FIGS. 2 and 5, there is shown one embodiment of a tip portion of the surgical needle of the present invention. The needle 10 undergoes a transition from its cross-sectional shape at region 24 (e.g., modified square or flat pressed circular) to a circular cross-section in tip portion 16. (Of course, if the body portion 14 has a circular cross-section then there is no transition.) The needle tip portion 16 has a circular cross-section which decreases progressively from its proximal end 24 to the blunt distal end 18 of the needle. The needle tip portion 16 terminates in a flat circular blunt head 18 which is configured to permit piercing of non-cutaneous or friable soft tissues of the body while preventing skin penetration of the gloved hand of an operator.

The head 18 has a flat circular shape that blends smoothly at its circumference with the outer surface of the tapered portion by a blend radius 26 such that there are no sharp edges at the needle tip. Thus the entire tapered tip portion 16 including flat blunt tip 18 has a continuously smooth outer surface lacking any discontinuities or sharp cutting edges. By utilizing flat blunt head 18, the penetration force of needle 10 needed to penetrate the gloved hand of an operator is significantly increased as compared to conventional sharp point needles and prior art blunt tip needles. Consequently, needle 10 significantly decreases the probability of skin penetration of the gloved hand of an operator.

Figure 6:
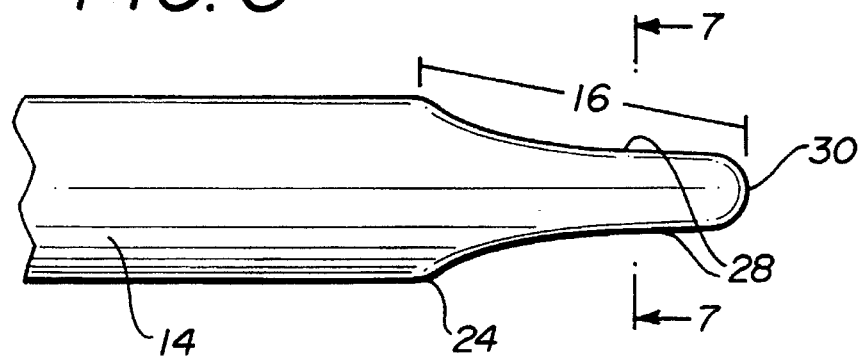
FIG. 6 is an enlarged fragmentary view of the tip portion of another embodiment of the present invention.
Figure 7:
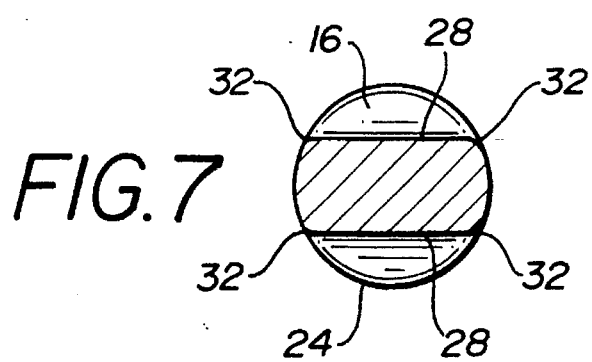
FIG. 7 is a cross-sectional view taken along lines 7—7 in FIG. 6.

Turning now to FIGS. 6 and 7, there is shown a tip portion of another embodiment of the present invention. In this embodiment, the needle 10 undergoes a transition from its cross-sectional shape at region 24 (e.g., circular, rectangular, square or modified square) to a flat pressed circular cross-section in tip 16 having two flat surfaces 28. If body 14 also has a flat pressed circular cross-section, then body 14 and tip portion 16 will have a uniform flat pressed circular cross-section throughout its entire length. The two flat surfaces 28 extend substantially the entire length of tip portion 16.

The flat pressed circular tip portion 16 terminates at blunt head 30 having a flat pressed circular dome shape. The curved blunt head 30 blends smoothly at its perimeter with the outer surface of the tip portion 16. In addition, the flat surfaces 28 blend smoothly with each other and with the rest of the outer surface of tip portion 16 by means of blend radii 32. As a result, the entire tip portion 16 has a continuously smooth outer surface lacking any discontinuities or sharp edges. The flat surfaces 28 in tip portion 16 along with the curved blunt head 30 significantly increases the penetration force needed to penetrate a gloved hand as compared to conventional sharp point needles and prior art blunt tip needles.

Figure 8:
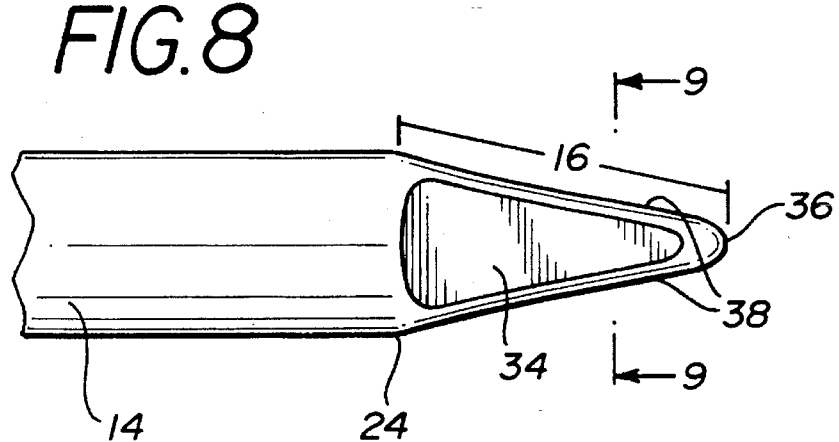
FIG. 8 is an enlarged fragmentary view of the tip portion of a further embodiment of the present invention.
Figure 9:
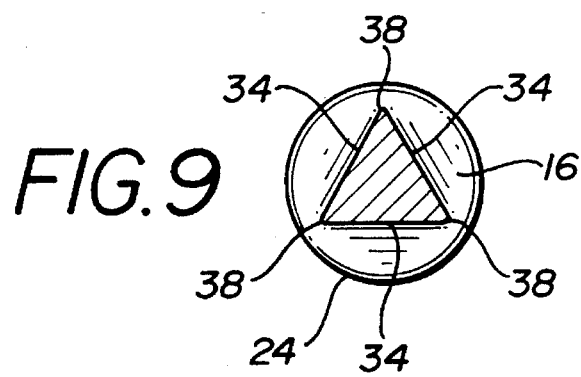
FIG. 9 is a cross-section view taken along lines 9—9 in FIG. 8.

A further embodiment of the tip portion of the present invention is shown in FIGS. 8 and 9. The needle 10 undergoes, at region 24, a gradual transition from its cross-sectional shape in body portion 14 (e.g., circular, rectangular, square, modified square or flat pressed circular) to a triangular cross-sectional shape in tip 16 having three flat surfaces 34. The three flat surfaces 34 extend substantially the entire length of tip portion 16. The tip portion has a triangular cross-section which progressively decreases from proximal end 24 to blunt tip 36.

The blunt tip 36 has a triangular dome shape that blends smoothly at its perimeter with the outer surface of tip portion 16. The flat surfaces 34 blend smoothly between each other and with the outside surface of tip portion 16 by means of blend radii 38. This results in a substantially triangular cross-sectional tip portion 16 having rounded corners to provide a smooth outer surface. Accordingly, the entire tip portion 16 has a continuously smooth outer surface lacking any discontinuities or sharp edges. The use of the flat surfaces 34 along with blunt head 36 significantly increases the penetration force needed to penetrate a gloved hand as compared to conventional sharp point needles and prior art blunt tip needles.

The surgical needles of the present invention may also be constructed with a tip portion in the shape of a polygon having more than three surfaces or any other suitable configuration of flat surfaces to achieve the advantageous results described above.

EXAMPLE I

A comparison test was made in which prior art blunt tip needles having a rounded tip and needles of the present invention having three flats on the side and a rounded tip were both caused to penetrate 0.45 mm thick PORVAIR®. PORVAIR® is a well known synthetic membrane that simulates tissue for needle testing. The results are shown in the following table showing the force in grams required to penetrate.

TABLE 1

|  |  | PENETRATION # | | |
|---|---|---|---|---|
|  |  | 1 | 2 | 3 |
| PRIOR ART NEEDLE | 1 | 460 | 470 | 473 |
|  | 2 | 435 | 475 | 458 |
|  | 3 | 417 | 455 | 445 |
| TRI-FLAT NEEDLE | 1 | 377 | 427 | 420 |
|  | 2 | 385 | 398 | 393 |
|  | 3 | 362 | 396 | 463 |

The average force for the prior art needle was 454 grams while the average force for the tri-flat needle of the present invention was 402. Thus, where both needles had rounded blunt tips to protect against penetration of the glove, the needle of the present invention required significantly less force to penetrate tissue and thus, will not have sufficient momentum after tissue penetration to cause the penetration of the glove.

EXAMPLE II

A comparison test was made in which prior art blunt tip needles having a rounded tip and needles of the present invention having a single flat surface on the end of the tip were both caused to penetrate 1.1 mm PROVAIR®. Four different needles in accordance with the present invention were used each having a different percentage of the ratio of the diameter of the flat end as compared to the diameter of the total cross-section of the needle. Thus, the 13% needle has the smallest diameter flat surface on the tip and the 51% needle has the largest diameter of the flat surface on the tip. The results of the comparison tests are shown in the following table.

TABLE 2

Prior Art Needle
NEEDLE CODE: 483972
NEEDLE TYPE: CT-1B
LOT #: 3E0220

|  | PENETRATIONS | | | | | | |
|---|---|---|---|---|---|---|---|
| NEEDLE | 1 | 2 | 3 | 4 | 5 | AVG 5 | STD 5 |
| 1 | 1060 | 1139 | 1210 | 1339 | 1338 | 1217 | 123 |
| 2 | 1051 | 1138 | 1238 | 1324 | 1437 | 1238 | 152 |
| 3 | 977 | 999 | 1118 | 1218 | 1403 | 1143 | 175 |
| 4 | 1065 | 1240 | 1421 | 1528 | 1580 | 1367 | 213 |
| 5 | 873 | 900 | 1092 | 1211 | 1343 | 1084 | 201 |
| AVG. | 1005 | 1083 | 1216 | 1324 | 1420 |  |  |
| S.D. | 82 | 134 | 130 | 128 | 99 |  |  |
| AVERAGE OF 5 PENETRATIONS |  |  |  |  |  | 1210 |  |
| STD. DEV. BETWEEN NEEDLES |  |  |  |  |  | 107 |  |

TABLE 2-continued

13% RATIO FLAT TIP NEEDLE
NEEDLE TYPE: CT-1B, #0871

|  | PENETRATIONS | | | | | | |
|---|---|---|---|---|---|---|---|
| NEEDLE | 1 | 2 | 3 | 4 | 5 | AVG 5 | STD 5 |
| 1 | 420 | 880 | 632 | 1060 | 1060 | 810 | 280 |
| 2 | 880 | 922 | 937 | 1020 | 1073 | 966 | 78 |
| 3 | 938 | 996 | 1101 | 1250 | 1448 | 1147 | 206 |
| 4 | 888 | 918 | 993 | 1098 | 1213 | 1022 | 134 |
| 5 | 942 | 1017 | 1088 | 1130 | 1208 | 1077 | 102 |
| AVG. | 814 | 947 | 950 | 1112 | 1200 |  |  |
| S.D. | 222 | 58 | 190 | 88 | 156 |  |  |
| AVERAGE OF 5 PENETRATIONS |  |  |  |  |  | 1004 |  |
| STD. DEV. BETWEEN NEEDLES |  |  |  |  |  | 127 |  |

27% FLAT TIP NEEDLE
UNIT: NEW BLACK
MEDIA: 1.1 mm PORVAIR CINN.
DATE: 6/1/93

|  | PENETRATIONS | | | | | | |
|---|---|---|---|---|---|---|---|
| NEEDLE | 1 | 2 | 3 | 4 | 5 | AVG 5 | STD 5 |
| 1 | 885 | 940 | 983 | 1118 | 1198 | 1025 | 130 |
| 2 | 837 | 944 | 1068 | 1203 | 1215 | 1053 | 164 |
| 3 | 807 | 908 | 992 | 1118 | 1303 | 1026 | 193 |
| 4 | 779 | 812 | 900 | 910 | 1183 | 917 | 159 |
| 5 | 808 | 832 | 938 | 1021 | 1162 | 952 | 145 |
| AVG. | 823 | 887 | 976 | 1074 | 1212 |  |  |
| S.D. | 40 | 62 | 63 | 112 | 54 |  |  |
| AVERAGE OF 5 PENETRATIONS |  |  |  |  |  | 995 |  |
| STD. DEV. BETWEEN NEEDLES |  |  |  |  |  | 57 |  |

38% FLAT TIP NEEDLE
NEEDLE TYPE: CT-1B, #3034

|  | PENETRATIONS | | | | | | |
|---|---|---|---|---|---|---|---|
| NEEDLE | 1 | 2 | 3 | 4 | 5 | AVG 5 | STD 5 |
| 1 | 900 | 943 | 1008 | 1112 | 1060 | 1005 | 86 |
| 2 | 742 | 785 | 828 | 946 | 980 | 856 | 103 |
| 3 | 830 | 926 | 980 | 1100 | 1153 | 998 | 131 |
| 4 | 783 | 860 | 860 | 933 | 973 | 882 | 74 |
| 5 | 793 | 872 | 900 | 1048 | 1038 | 930 | 110 |
| AVG. | 810 | 877 | 915 | 1028 | 1041 |  |  |
| S.D. | 59 | 62 | 77 | 84 | 73 |  |  |
| AVERAGE OF 5 PENETRATIONS |  |  |  |  |  | 934 |  |
| STD. DEV. BETWEEN NEEDLES |  |  |  |  |  | 67 |  |

51% FLAT TIP NEEDLE
NEEDLE TYPE: CT-1B, #3410

|  | PENETRATIONS | | | | | | |
|---|---|---|---|---|---|---|---|
| NEEDLE | 1 | 2 | 3 | 4 | 5 | AVG 5 | STD 5 |
| 1 | 690 | 850 | 968 | 1135 | 1230 | 975 | 217 |
| 2 | 683 | 790 | 934 | 1000 | 1100 | 901 | 166 |
| 3 | 645 | 680 | 793 | 920 | 1018 | 811 | 158 |
| 4 | 707 | 740 | 842 | 940 | 1040 | 854 | 139 |
| 5 | 674 | 748 | 866 | 963 | 1086 | 867 | 165 |
| AVG. | 680 | 762 | 881 | 992 | 1095 |  |  |
| S.D. | 23 | 63 | 70 | 86 | 83 |  |  |
| AVERAGE OF 5 PENETRATIONS |  |  |  |  |  | 882 |  |
| STD. DEV. BETWEEN NEEDLES |  |  |  |  |  | 61 |  |

The surprising results here were that the 51% needle required the least amount of force to penetrate PORVAIR® as compared with the other flat tip needles. Each of the flat tip needles of the present invention required less force to penetrate the PORVAIR® but is sufficiently blunt to provide a decreased risk of penetration through the glove than a sharp point needle or prior art blunt tip needles.

It is perceived that the blunt needle of the present invention may, in addition to reducing the risk of infectious disease transmission by reducing the risk of an accidental needle stick, also serve to reduce the risk of needle contamination by reducing the amount of bleeding caused by the needle. Decreased bleeding occurs because the blunt needle is more likely to simply push blood vessels aside rather than penetrate them as it is being advanced in the body.

While the invention has been particularly shown and described with respect to illustrative and preferred embodiments thereof, it will be understood by those skilled in the art that the foregoing and other changes in form and details may be made therein without departing from the spirit and scope of the invention which should be limited only the scope of the appended claims.

What is claimed is:

1. A surgical needle comprising:
   a tip portion having a blunt tip at a distal end thereof and at least one flat surface on the distal end of the tip portion, said flat surface blending smoothly with an outer surface of said tip portion such that the tip portion has a continuously smooth outer surface lacking any discontinuities or sharp cutting edges, and wherein said cross-sectional is circular and said blunt tip has a flat circular shape.

2. The surgical needle according to claim 1, further including a suture mounting portion having a hole to which a suture is to be attached and a body portion which is disposed between and contiguous with said suture mounting portion and said tip portion.

3. The surgical needle according to claim 2, wherein said needle has an overall curved shaped with a constant radius of curvature.

4. The surgical needle according to claim 2, wherein said body portion has a generally uniform cross-sectional area throughout an entire length thereof.

5. The surgical needle according to claim 4, wherein said cross-sectional area of said body portion has a shape selected from the shape consisting of circular, square, modified square, rectangular and flat pressed circular.

* * * * *